(12) United States Patent
O'Day

(10) Patent No.: US 9,629,980 B2
(45) Date of Patent: Apr. 25, 2017

(54) VARIABLE STIFFNESS CATHETER, INTRALUMINAL TREATMENT SYSTEM, AND METHOD

(75) Inventor: Therese J. O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 573 days.

(21) Appl. No.: 13/989,499

(22) PCT Filed: Sep. 23, 2011

(86) PCT No.: PCT/US2011/052859
§ 371 (c)(1),
(2), (4) Date: May 24, 2013

(87) PCT Pub. No.: WO2012/071105
PCT Pub. Date: May 31, 2012

(65) Prior Publication Data
US 2013/0245551 A1    Sep. 19, 2013

Related U.S. Application Data

(60) Provisional application No. 61/416,805, filed on Nov. 24, 2010.

(51) Int. Cl.
*A61M 25/04* (2006.01)
*A61M 25/01* (2006.01)
*A61M 25/00* (2006.01)

(52) U.S. Cl.
CPC .... *A61M 25/0102* (2013.01); *A61M 25/0053* (2013.01); *A61M 25/04* (2013.01); *A61M 2025/0063* (2013.01)

(58) Field of Classification Search
CPC .......... A61M 25/0102; A61M 25/0053; A61M 25/04; A61M 25/0108; A61M 2025/0063;
(Continued)

(56) References Cited

U.S. PATENT DOCUMENTS 4,248,234 A   2/1981 Assenza et al.
4,498,473 A   2/1985 Gereg
(Continued)

FOREIGN PATENT DOCUMENTS

| WO | WO 9906097 A1 * | 2/1999 | ............ A61M 29/00 |
|----|-----------------|--------|------------------------|
| WO | 2008101080      | 8/2008 |                        |
| WO | 2009142821      | 11/2009|                        |

OTHER PUBLICATIONS

Foam Definition, Merriam-Webster Inc, 2015.*

*Primary Examiner* — Aarti B Berdichevsky
(74) *Attorney, Agent, or Firm* — Liell & McNeil

(57) ABSTRACT

A variable stiffness catheter includes an elongate tubular body having proximal and distal body ends and defining a lumen extending longitudinally between a fluid inlet in the proximal body end and a fluid outlet in the distal body end. The catheter includes a vacuum responsive stiffener coupled with the elongate tubular body, which may include a stiffening medium such as an open cell foam having an expanded state and a vacuum collapsed state. The stiffening medium can transition between the expanded state at which it is relatively flexible and the vacuum collapsed state at which it is relatively inflexible via withdrawing fluid from the vacuum responsive stiffener by way of a vacuum device.

19 Claims, 3 Drawing Sheets

(58) Field of Classification Search
CPC ............... A61M 25/005; A61M 25/01; A61M 25/0105; A61M 25/0141; A61M 25/0155; A61M 2025/0065
See application file for complete search history.

(56) References Cited

U.S. PATENT DOCUMENTS

| | | | |
|---|---|---|---|
| 4,693,257 A * | 9/1987 | Markham | 600/565 |
| 4,768,858 A * | 9/1988 | Hussein | A61B 1/00165 |
| | | | 385/118 |
| 4,771,776 A * | 9/1988 | Powell et al. | 606/194 |
| 4,815,450 A * | 3/1989 | Patel | A61B 1/00078 |
| | | | 600/115 |
| 5,718,669 A | 2/1998 | Marble | |
| 6,032,077 A | 2/2000 | Pomeranz | |
| 6,884,233 B2 * | 4/2005 | Dance et al. | 604/101.03 |
| 7,766,896 B2 | 8/2010 | Kornkven Volk et al. | |
| 2003/0032859 A1 | 2/2003 | Belson | |
| 2006/0069346 A1 | 3/2006 | Smith et al. | |
| 2006/0211979 A1 | 9/2006 | Smith et al. | |
| 2008/0140098 A1 * | 6/2008 | Kumar et al. | 606/153 |
| 2008/0200762 A1 | 8/2008 | Stokes et al. | |
| 2009/0292172 A1 | 11/2009 | Roskopf et al. | |

\* cited by examiner

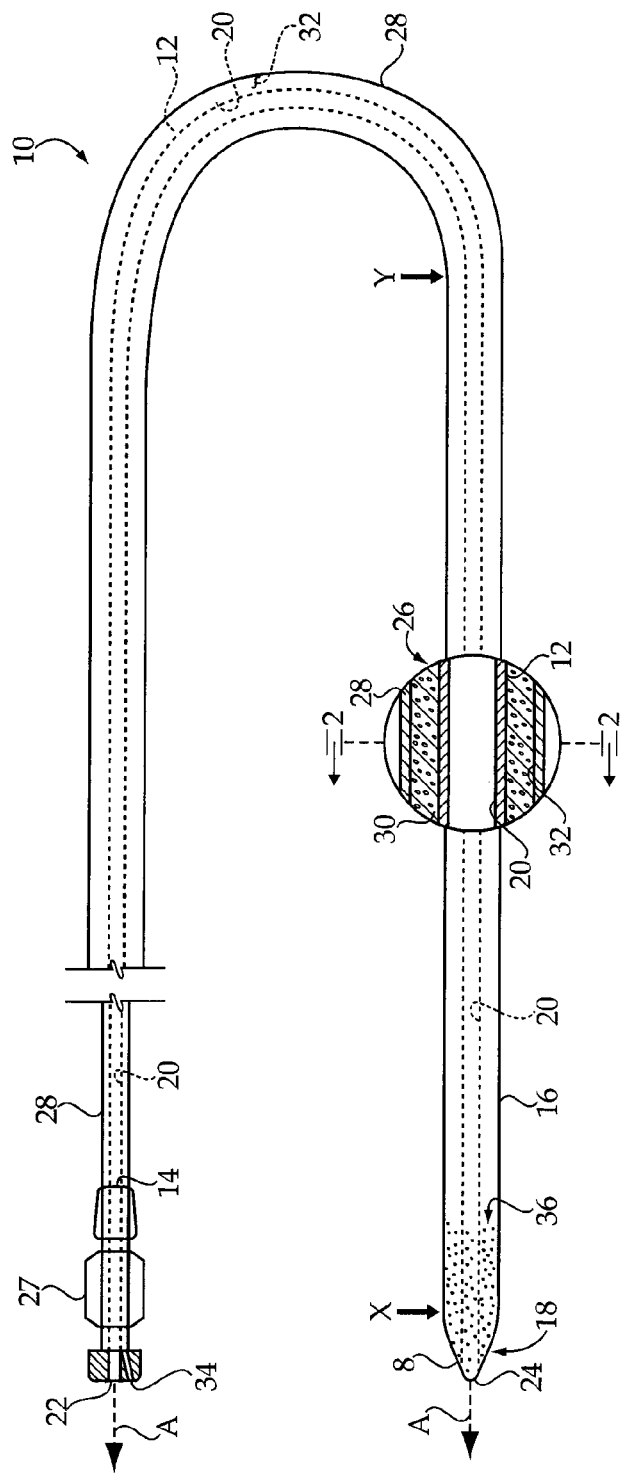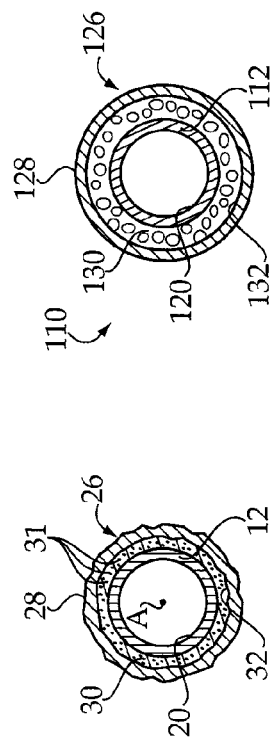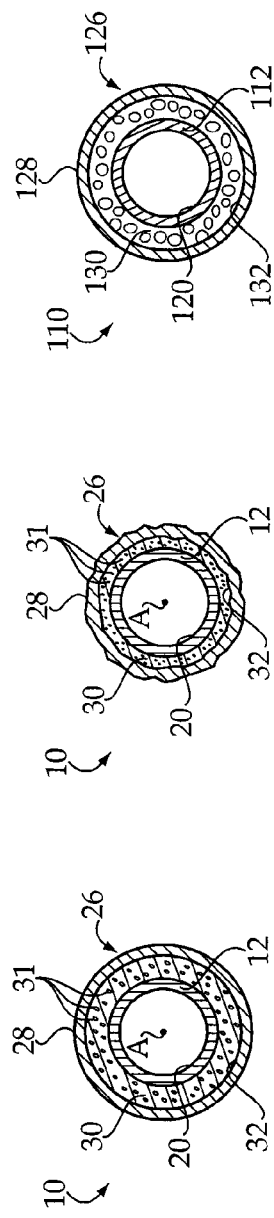
Figure 1
Figure 2
Figure 3
Figure 4

VARIABLE STIFFNESS CATHETER, INTRALUMINAL TREATMENT SYSTEM, AND METHOD

This Application is a National Stage of PCT/US2011/052859, filed Sep. 23, 2011, which claimed the benefit of the filing date of U.S. Provisional Application Ser. No. 61/416,805, filed Nov. 24, 2010.

TECHNICAL FIELD

The present disclosure relates generally to catheters for use in intraluminal procedures, and relates more particularly to stiffening a catheter within a body lumen of a patient by withdrawing a fluid from a stiffener coupled with an elongate catheter body.

BACKGROUND

A wide variety of catheters and the like are used for accessing different body lumens in patients, and are used in a large number of different types of procedures. Infusion catheters are well known and widely used for delivering treatment agents into the vascular system or other parts of a patient's body for the treatment of thrombi, tumors, and various other types of undesired tissue or abnormalities. Catheters are also used for introducing contrast agents or dyes, and in the placement of intraluminal treatment devices such as filters and stents. Still other examples of the wide applicability of catheters in medical technology include providing an access pathway for embolization mechanisms, angioplasty devices, and even cutting tools and cameras.

Various entry techniques and pathways may be used to access treatment locations within a body lumen of a patient. Percutaneous access to the cardiovascular system for peripheral intervention techniques is one well known example, and typically involves forming an access opening in a patient's skin, and then guiding a catheter by way of a wire guide through the vasculature while manipulating the wire guide and catheter from a location outside of the patient's body. Once a target location is reached, the catheter may be used in whole or in part to conduct the example procedures mentioned above. Related, but somewhat varying techniques are used to access other body lumens such as the bladder, biliary ducts, etc. A clinician is typically unable to know precisely where a catheter is presently located within a patient without some external mechanism such as an imaging device which enables in vivo visualization on a monitor or the like. Despite a high level of skill among many clinicians, as well as the availability of sophisticated catheter guiding and imaging techniques, properly placing a catheter for delivery of a contrast agent, introduction of a treatment device, or for that matter any other purpose, is still often a tricky endeavor. Even once placed, it is common for catheters or the like to be relatively difficult to maintain in position within the patient.

SUMMARY OF THE DISCLOSURE

In one aspect, a variable stiffness catheter includes an elongate tubular body having proximal and distal body ends, and defining a lumen extending longitudinally between a fluid inlet located in the proximal body end and a fluid outlet located in the distal body end. The variable stiffness catheter further includes a vacuum responsive stiffener coupled with the elongate tubular body.

In another aspect, a method of performing an intraluminal procedure on a patient includes advancing a catheter having an elongate tubular body through a body lumen of a patient, and stiffening the catheter at least in part by withdrawing a fluid from a stiffener coupled with the elongate tubular body. The method further includes fluidly connecting the body lumen with a fluid reservoir located outside of the patient by way of a longitudinally extending lumen within the elongate tubular body.

In still another aspect, an intraluminal treatment system includes a catheter having an elongate tubular body with proximal and distal body ends, and defining a lumen extending longitudinally between a fluid inlet located in the proximal body end and a fluid outlet located in the distal body end. The system further includes a vacuum responsive stiffener coupled with the elongate tubular body, and a vacuum device connectable with the vacuum responsive stiffener.

BRIEF DESCRIPTION OF THE DRAWINGS

FIG. 1 is a partially sectioned side diagrammatic view, including a detailed enlargement, of a variable stiffness catheter according to one embodiment;

FIG. 2 is a sectioned view taken along line 2-2 of FIG. 1;

FIG. 3 is a sectioned view similar to FIG. 2 showing the catheter in a stiffened state;

FIG. 4 is a sectioned view similar to FIG. 2 of a variable stiffness catheter according to another embodiment;

DETAILED DESCRIPTION

Figure 5:
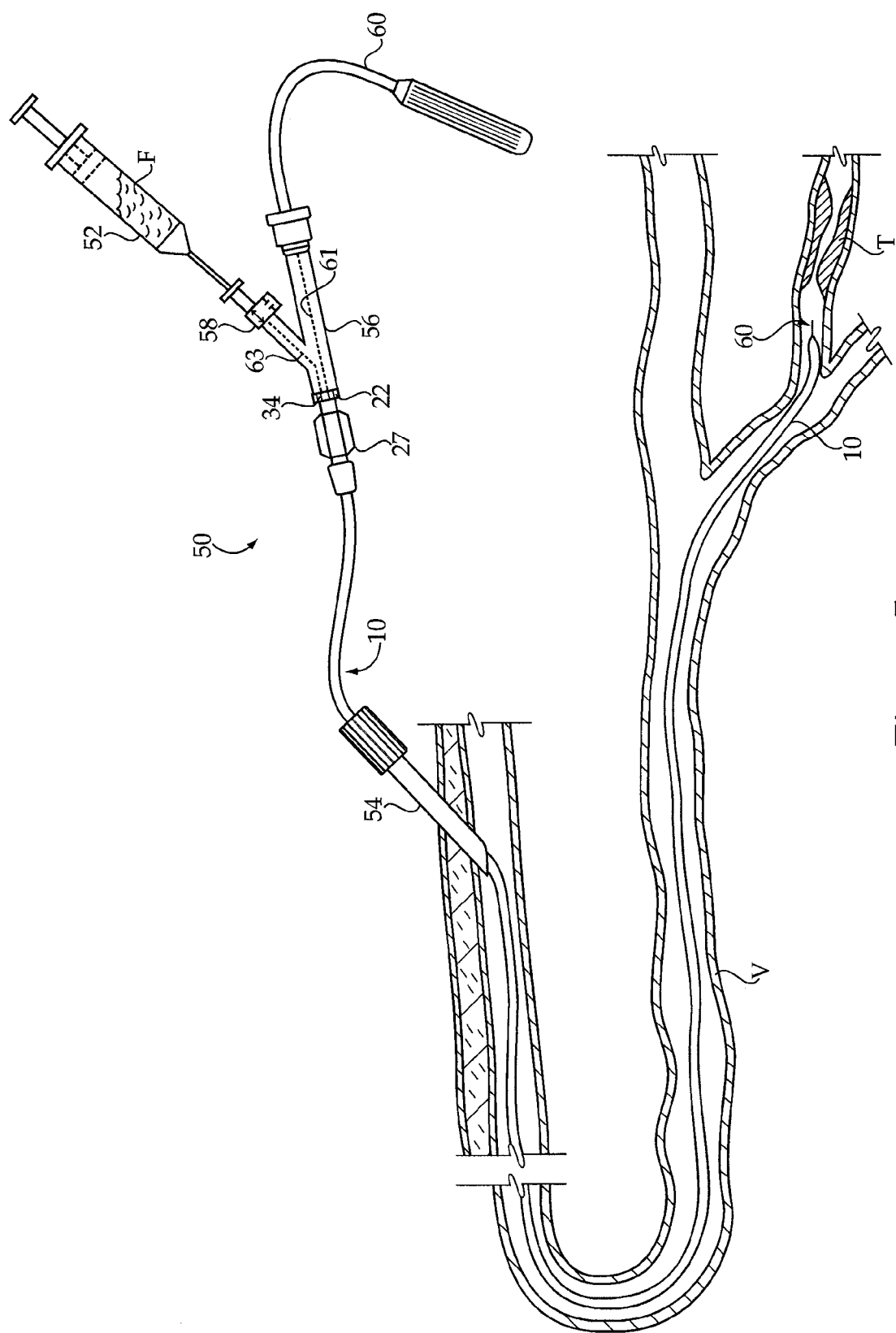
FIG. 5 is a side diagrammatic view of an intraluminal treatment system at one stage of an intraluminal treatment procedure, according to one embodiment.

Referring to FIG. 1, there is shown a variable stiffness catheter 10 according to one embodiment. Catheter 10 may include an elongate tubular body 12 having a proximal body end 14, and a distal body end 16 having a distal tip 18. Distal tip 18 may include a distally narrowing taper 8, and has a fluid outlet 24 formed therein. A fluid inlet 22 is located in proximal body end 14, and body 12 defines a lumen 20 extending longitudinally between fluid inlet 22 and fluid outlet 24. In one embodiment, distal tip 18 may be formed from or impregnated with a radiopaque material 36. Lumen 20 defines a longitudinal axis A of elongate tubular body 12 extending between proximal body end 14 and distal body end 16.

Catheter 10 may further include a vacuum responsive stiffener 26 coupled with elongate tubular body 12. In one embodiment, elongate tubular body 12 may include an inner tubular body, and stiffener 26 may include an outer tubular body 28 positioned about and coaxial with inner tubular body 12. A cavity 32 may extend between inner tubular body 12 and outer tubular body 28, and may include a generally cylindrical cavity centered about longitudinal axis A and extending from proximal body end 14 to distal tip 18. In one practical implementation strategy, cavity 32 may be closed within distal body end 16 such as at an attachment location of distal tip 18, a point shown approximately via arrow X. Cavity 32 may fluidly connect with a port 34 formed in a manifold 27 coupled with or comprising a part of proximal body end 14. Fluid inlet 22 may also be formed in manifold 27, such that separate and independent fluid connections may be made to lumen 20 and to cavity 32 from a location outside of the patient, for purposes which will be apparent from the following description.

A stiffening medium 30 may be disposed between inner tubular body 12 and outer tubular body 28, and positioned within cavity 32 such that stiffening medium 30 surrounds inner tubular body 12 within cavity 32. In the embodiment shown, stiffening medium 30 extends within cavity 32 approximately between a first location shown via arrow Y in catheter 10, and a second location shown via arrow X. It will thus be understood that a portion of cavity 32 may be filled or substantially filled with stiffening medium 30, extending approximately between the arrows Y and X, whereas another portion of cavity 30 may be free of, or substantially free of, stiffening medium 30. According to such a construction, the portion of cavity 32 extending approximately from arrow Y in a proximal direction to port 34 may serve as a fluid lumen for supplying or withdrawing a fluid respectively to or from stiffening medium 30 in a manner further described herein. In other embodiments, stiffening medium 30 might fill all of cavity 32.

Referring also now to FIG. 2, there is shown a sectioned view taken along line 2-2 of FIG. 1. In one embodiment, stiffening medium 30 may include a porous medium attached to at least one of inner tubular body 12 and outer tubular body 28, and having each of an expanded state and a vacuum collapsed state. In one practical implementation strategy, stiffening medium 30 may include an open cell foam such as a foamed polyurethane material. In an alternative embodiment shown in FIG. 4, a variable stiffness catheter 110 includes an elongate tubular body 112 comprising an inner tubular body and defining a longitudinally extending lumen 120, and including a vacuum responsive stiffener 126 functionally similar to stiffener 26 but having certain differences. In particular, stiffener 126 may include a stiffening medium 130 within a cavity 132 extending between inner tubular body 112 and an outer tubular body 128, but instead of a foam material as in catheter 10, stiffening medium 130 may include a plurality of beads.

As mentioned above, stiffening medium 30 may include a porous medium, and having a relatively flexible expanded state and a relatively inflexible vacuum collapsed state. The expanded state may include a rest state of stiffening medium 30, whereas the vacuum collapsed state. As shown in FIGS. 2 and 3, lumen 20 retains an expanded cross section when the catheter is in both the flexible state and stiff state respectively may include a biased state assumed by stiffening medium 30 when a vacuum is applied to cavity 32. Referring to FIG. 3 in comparison to FIG. 2, there is shown catheter 10 as it might appear when stiffening medium 30 has been partially or fully collapsed by withdrawing a fluid such as air or saline from cavity 32. It may be noted that stiffening medium 30 has collapsed or squeezed inward in a radial direction about longitudinal axis A such that outer tubular body 28 is slightly shrunk radially about inner tubular body 12. Depending upon the materials and construction selected for catheter 10, physical deformation of outer tubular body 28 and/or inner tubular body 12 may or may not occur and may or may not be visible to the naked eye. Normally open pores or cells 31 in stiffening medium 30 may nevertheless be expected to shrink or close when fluid is withdrawn from cavity 32 under vacuum. As a result of applying a vacuum to cavity 32 and withdrawing fluid, stiffening medium 30 transitions from its relatively flexible expanded state to its relatively inflexible vacuum collapsed state, the significance of which will be further apparent from the following description.

A similar phenomenon can be expected to occur using the embodiment shown in FIG. 4, wherein withdrawal of fluid from cavity 132 can be expected to deform outer tubular body 128 radially inwardly about inner tubular body 112, such that the beads, for example glass or plastic beads, comprising stiffening medium 130 begin to provide structural reinforcement or increased structural reinforcement between inner and outer tubular bodies 112 and 128 and thereby stiffen catheter 110.

As mentioned above, stiffening medium 30 may include an open cell foam such as a foamed polyurethane. In one practical implementation strategy, catheter 10 may be made by way of a process which includes curing a liquid polyurethane material in contact with inner tubular body 12. For instance, inner tubular body 12 may be dipped in or sprayed with an activated polymerizing polyurethane starting material containing, or to which is added, a blowing or foaming agent, and then the resulting polyurethane material allowed to cure. Inner tubular body 12 having the cured, foamed polyurethane coating may then be slid into outer tubular body 28 and the respective tubular bodies attached via any suitable procedure to render an assembly of inner and outer tubular bodies 12 and 28 and stiffening medium 30. An end of cavity 32 which is to comprise the closed distal end of cavity 32 near arrow X may then be closed or sealed via a suitable sealing material, or for instance by melting material of inner tubular body 12 to material of outer tubular body 28, and distal tip 18 attached. Stiffening medium 30 may optionally be mechanically or chemically attached to inner tubular body 12 by way of the reaction and curing process which forms stiffening medium 30, depending upon the materials or physical surface properties such as roughness. Other strategies for attaching stiffening medium 30 to one or both of inner tubular body 12 and outer tubular body 28 are contemplated herein, such as by way of suitable adhesives. Each of inner and outer tubular bodies 12 and 28 may be formed from biocompatible materials conventionally used in the extrusion of elongate tubular bodies for intraluminally placeable catheters. Nylon materials, fluoropolymers and other suitable materials are well known and widely used. Catheter 110 may be made by a process in which the beads comprising stiffening medium 130 are poured into cavity 132 or otherwise carried into cavity 132 such as by way of a fluid. Manifold 27 may be coupled with each of inner and outer tubular bodies 12 and 28, or in the case of catheter 110 inner and outer tubular bodies 112 and 128, to render the completed variable stiffness catheter.

INDUSTRIAL APPLICABILITY

Turning now to FIG. 5, there is shown an intraluminal treatment system 50 at one stage in performing an intraluminal treatment procedure on a patient. Intraluminal treatment system 50 is shown using catheter 10, having been passed by way of an introducer sheath 54 into a body lumen V of a patient. Catheter 110 and other catheter embodiments contemplated herein might similarly be used, and thus the present description should be understood to generically describe an example use of catheters within the context of the present disclosure. In the illustrated embodiment, introducer sheath 54 has passed through an opening in the patient's skin and provides access to a body lumen V such as a vein or artery. Catheter 10 has been advanced through body lumen V through one or more turns and/or junctions, and is positioned in proximity to a treatment site T such as a thrombus or the like. A wire guide 60 is shown extending through catheter 10 as it might appear where catheter 10 has been advanced in an over-the-wire manner to the desired location within body lumen V. Wire guide 60 may extend through lumen 20, but in other versions (not shown) might pass through a relatively short wire guide lumen formed in or near distal tip 18 for rapid exchange applications, or through a second lumen extending all the way through body 12 in parallel with lumen 20.

In FIG. 5, a fitting 56 is shown coupled with manifold 27, and provides one access passage 61 for wire guide 60 to lumen 20, and another access passage 63 for fluidly connecting a vacuum device 52 with cavity 32 by way of a valve 58. It will thus be understood from FIG. 5 that wire guide 60 may pass through fluid inlet 22 in manifold 27, whereas a fluid connection between vacuum device 52 and cavity 32 may be established by way of port 34. In FIG. 5, valve 58 is shown in an open position as it might appear where vacuum device 52 is being used to withdraw a fluid F from cavity 32 to adjust stiffening medium 30 within catheter 10 from its relatively flexible state to its relatively inflexible state in the manner described herein. While vacuum device 52 has been depicted as withdrawing fluid while wire guide 60 is positioned within catheter 10, this need not always be the case, and in some instances might even be disfavored. In other words, wire guide 60 might be withdrawn from catheter 10 prior to commencing withdrawing fluid from cavity 32 by way of vacuum device 52.

In the illustrated embodiment, vacuum device 52 is shown as a conventional manually operable syringe, however, in other embodiments a different type of device such as a motorized vacuum device or pump might be used. It may also be noted that fluid F is shown as a liquid. It may be desirable in some instances to withdraw air from cavity 32 and thus stiffening mechanism 26, and replace the air with a suitable liquid such as saline, prior to advancing catheter 10 through the body lumen as shown. Substituting a liquid F for the air normally residing in cavity 32 and stiffening medium 30 might be performed by applying a vacuum to port 34 with catheter 10 positioned outside of the patient, and then injecting a liquid back into cavity 32, prior to commencing advancing catheter 10 through the body lumen. In still other embodiments, the fluid withdrawn from catheter 10 to stiffen the same may simply be air and no substitution of a liquid needed.

Figure 6:
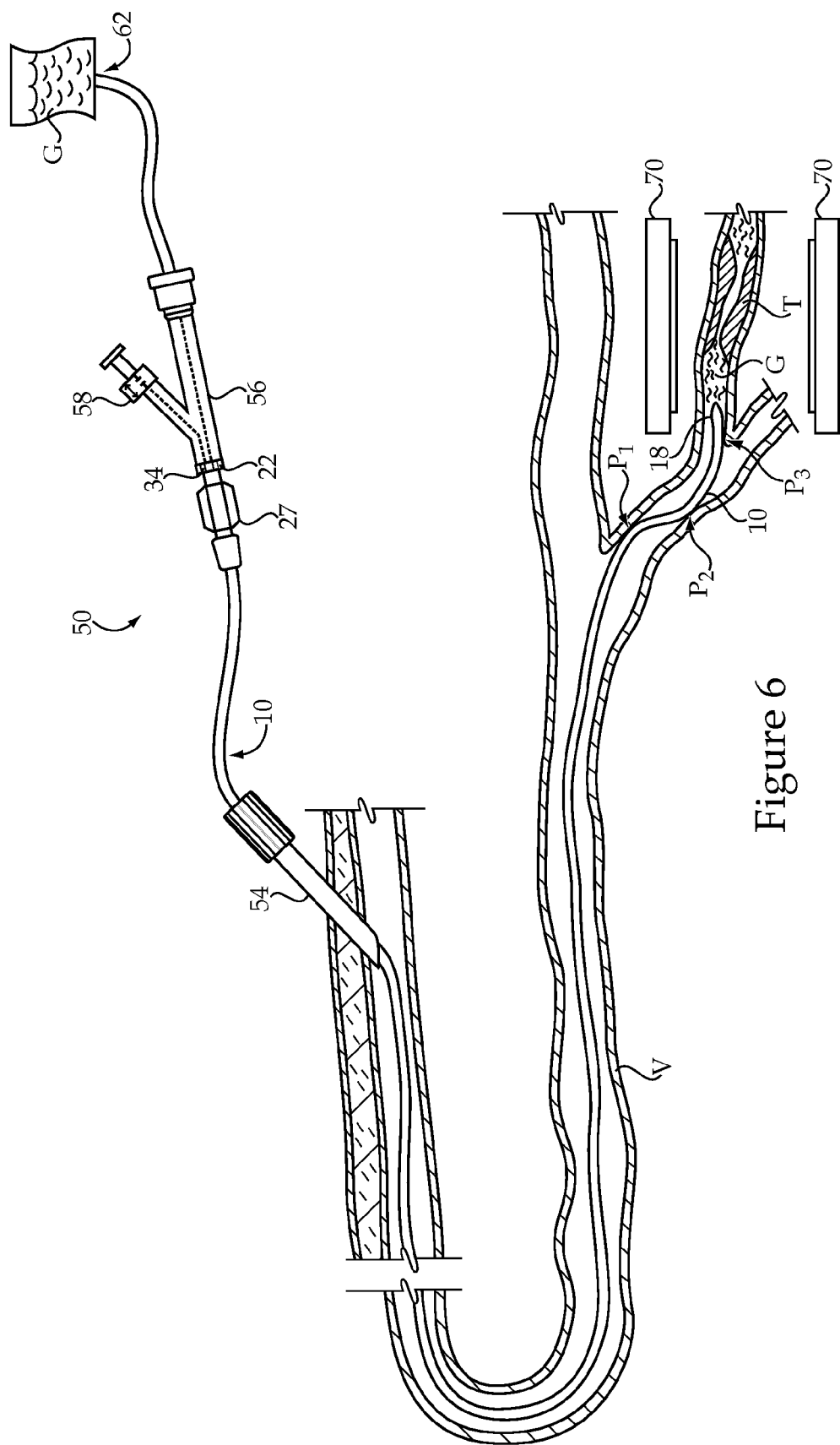
FIG. 6 is a side diagrammatic view of the intraluminal treatment system of FIG. 5 at another stage of the intraluminal treatment procedure.

Referring also now to FIG. 6, there is shown system 50 as it might appear at another stage of an intraluminal treatment procedure. In FIG. 6, a fluid reservoir 62 is positioned outside the patient and contains another fluid G, and is shown connected with fitting 56 as it might appear were in fluid communication with lumen 20, and thus in fluid communication with body lumen V. In one embodiment, fluid reservoir 62 may contain a liquid contrast agent, a variety of which are well known and widely used. Valve 58 has been adjusted from an open position shown in FIG. 5 to a closed position after withdrawing fluid F from catheter 10, such that catheter 10 is in a relatively stiff state within body lumen V. An imaging system 70 is shown positioned such that imaging by way of radiography or the like of treatment location T may occur. Fluid G is also shown exiting distal tip 18. Fluid reservoir 62 might be equipped with a pressure cuff or the like, or an infusion pump used, to enable injecting liquid G into body lumen V as desired.

It has been discovered that an exit pressure of fluid from a catheter tip within a body lumen, such as an exit pressure of a liquid containing a contrast agent or the like, can cause the associated catheter to be displaced within the body lumen. In other words, when conveying a fluid from a fluid reservoir located outside of a patient to a body lumen, a back pressure of the exiting fluid on the catheter can cause the catheter to shift from a desired location and/or orientation within the body lumen. One mechanism specifically responsible for losing location is believed to be a straightening of a curved catheter in response to shifting back from a location just beyond a curve or junction. Since a catheter may have some bias towards a straight shape, once a point of contact with a patient's vasculature which is holding the catheter curved is lost, the catheter may revert to being more or less straight, ending up with the catheter tip out of place. In some instances, the displacement of the catheter may be such that injection of contrast agent or the like occurs into a portion of the body lumen different from that which is targeted. Thus, where imaging of a treatment site is desired a catheter injecting liquid contrast agent can actually be displaced so that the contrast agent does not enter the portion of the body lumen which is desired to be imaged, and instead goes someplace else. Repositioning of the catheter and repeated injections of contrast agent were often previously necessary to ameliorate this problem. The present disclosure enables displacing of a catheter to be limited or eliminated altogether in response to fluid exit pressure such that imaging or other intraluminal treatment or diagnostic procedures can take place without the aforementioned problems.

In FIG. 6, a plurality of contact points, $P_1$, $P_2$ and $P_3$ are shown between catheter 10 and the inner walls of body lumen V. It is believed that stiffening catheter 10 in the manner described herein can effectively lock catheter 10 into position within body lumen V by way of contact with the inner walls thereof, and thus when contrast agent is injected stiffened catheter 10 will resist displacement. With prior art techniques, catheter tip 18 could be expected to be at risk of slipping back, catheter 10 straightening, and losing contact point $P_3$ such that contrast agent would be injected through the lower branch of lumen V rather than the one containing treatment location/thrombus T.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For instance, while the present description focuses on application to imaging, alternative or supplemental treatment procedures may be advantageously performed according to the teachings set forth herein. Once a treatment site is imaged, various procedures may be performed to actually treat undesired tissues or conditions of the patient such as stent placement, thrombolysis, angioplasty, and still others. Each of these procedures may benefit in at least certain instances from the availability of variable stiffness in a catheter, both as a navigational or positioning strategy to reach a target location, and as a means for stabilizing a catheter once a target location is reached. Thus, embodiments are contemplated in which a catheter is stiffened prior to reading a target location, then made more flexible, then possibly stiffened again. Variable stiffness in a catheter is contemplated to be advantageous anywhere a sharp curve or junction in the vascular system is to be navigated. Exemplary but non-limiting examples include reaching the ostium, gaining access to the carotids, and renal and pelvic procedures. Other aspects, features and advantages will be apparent upon an examination of the attached drawings and appended claims.

What is claimed is:

1. A method of performing an intraluminal procedure on a patient using a variable stiffness catheter that includes an elongate tubular body with proximal and distal body ends, and defining a longitudinal lumen extending between a fluid inlet located in the proximal body end and a fluid outlet located in the distal body end; and
- a vacuum responsive stiffener, which includes an open cell foam stiffening medium, coupled with the elongate tubular body, the method comprising the steps of:
- advancing the variable stiffness catheter having the elongate tubular body through a body lumen of a patient;
- stiffening the variable stiffness catheter at least in part by withdrawing a fluid from the open cell foam stiffening medium; and
- fluidly connecting the body lumen with a fluid reservoir located outside of the patient by way of the longitudinal lumen within the elongate tubular body;
- conveying a second fluid from the fluid reservoir to the body lumen by way of the longitudinally extending lumen, and limiting displacing the catheter during conveying the second fluid by way of the stiffening step.

2. The method of claim 1 wherein the step of limiting further includes limiting displacing the catheter in response to an exit pressure of the second fluid from the catheter.

3. The method of claim 2 wherein the step of conveying further includes conveying a contrast agent in the second fluid into the body lumen.

4. The method of claim 1 wherein the step of stiffening further includes withdrawing the fluid from a cavity between the elongate tubular body and an outer tubular body of the stiffener such that the open cell foam stiffening medium within the cavity transitions from a relatively flexible state to a relatively inflexible state.

5. The method of claim 4 wherein the step of stiffening further includes collapsing the open cell foam stiffening medium.

6. A variable stiffness catheter comprising:
- an elongate tubular body including proximal and distal body ends, and defining a lumen extending longitudinally between a fluid inlet located in the proximal body end and a fluid outlet located in the distal body end;
- a vacuum responsive stiffener, which includes an open cell foam stiffening medium, coupled with the elongate tubular body, and the vacuum responsive stiffener fills an elongated cylindrically shaped cavity at least partially defined by the elongate tubular body; and
- the lumen has an expanded cross section when the catheter is in a flexible state with a fluid in the open cell foam stiffening medium, and the lumen has the expanded cross section when the catheter is in a stiff state with the fluid out of the open cell foam stiffening medium.

7. The catheter of claim 6 wherein the distal body end includes a radiopaque tip, and wherein the fluid outlet is formed in the radiopaque tip.

8. The catheter of claim 6 wherein the elongate tubular body includes an inner tubular body, and wherein the vacuum responsive stiffener includes an outer tubular body positioned about the inner tubular body, and the open cell foam stiffening medium disposed between the inner and outer tubular bodies.

9. The catheter of claim 8 wherein a cavity extends between the inner and outer tubular bodies, and the open cell foam stiffening medium surrounds the inner tubular body within the cavity.

10. The catheter of claim 9 wherein the open cell foam stiffening medium includes a porous medium having an expanded state and a vacuum collapsed state.

11. The variable stiffness catheter of claim 8 wherein the catheter defines exactly one lumen, which is the lumen;
- the inner tubular body is concentric with the outer tubular body; and
- the lumen is defined by the inner tubular body.

12. An intraluminal treatment system comprising:
- a catheter having an elongate tubular body including proximal and distal body ends, and defining a lumen extending longitudinally between a fluid inlet located in the proximal body end and a fluid outlet located in the distal body end;
- a vacuum responsive stiffener, which includes an open cell foam stiffening medium, coupled with the elongate tubular body, and the vacuum responsive stiffener fills an elongated cylindrically shaped cavity at least partially defined by the elongate tubular body;
- a vacuum device connectable with the vacuum responsive stiffener;
- a wire guide positioned in the lumen and extending distally beyond the distal body end of the catheter; and
- the lumen has an expanded cross section when the catheter is in a flexible state with a fluid in the open cell foam stiffening medium, and the lumen has the expanded cross section when the catheter is in a stiff state with the fluid out of the open cell foam stiffening medium.

13. The intraluminal treatment system of claim 12 further comprising a fluid reservoir in fluid communication with the lumen.

14. The intraluminal treatment system of claim 13 wherein the fluid reservoir contains a liquid contrast agent, and further comprising a manifold fluidly connecting the fluid reservoir with the lumen and fluidly connecting the vacuum device with the vacuum responsive stiffener; and
- the fluid reservoir is pressurized to move the liquid contrasting agent toward the distal body end of the catheter.

15. The intraluminal treatment system of claim 12 wherein the elongate tubular body includes an inner tubular body, and wherein the vacuum responsive stiffener further includes an outer tubular body positioned about the inner tubular body, and the open cell foam stiffening medium between the inner and outer tubular bodies.

16. The intraluminal treatment system of claim 15 wherein the open cell foam stiffening medium includes a porous medium having a relatively flexible expanded state and a relatively inflexible vacuum collapsed state.

17. The intraluminal treatment system of claim 16 wherein the porous medium is in the expanded state and includes an open cell foam stiffening medium, and further comprising the fluid, which is a liquid, within the porous medium.

18. The intraluminal treatment system of claim 16 wherein the vacuum device includes a syringe.

19. The intraluminal treatment system of claim 18 wherein the catheter defines exactly one lumen, which is the lumen;
- the inner tubular body is concentric with the outer tubular body; and
- the lumen is defined by the inner tubular body.

* * * * *